United States Patent [19]

Cosyns et al.

[11] 4,409,410

[45] Oct. 11, 1983

[54] PROCESS FOR SELECTIVELY HYDROGENATING A DI-OLEFIN IN A MIXTURE OF HYDROCARBONS HAVING AT LEAST 4 CARBON ATOMS AND COMPRISING AN α-OLEFIN

[75] Inventors: Jean Cosyns, Maule; Daniel Durand, Rueil Malmaison, both of France

[73] Assignee: Institut Francais du Petrole, Ruell-Malmaison, France

[21] Appl. No.: 347,127

[22] Filed: Feb. 9, 1982

[51] Int. Cl.[3] ............................ C07C 5/06; C07C 5/16
[52] U.S. Cl. ...................................... 585/259; 585/262; 585/273; 585/275; 585/843; 252/460; 252/476; 208/143
[58] Field of Search ............... 585/259, 262, 273, 275; 252/460, 476; 208/143, 144

[56] References Cited

U.S. PATENT DOCUMENTS 4,126,645  11/1978  Collins ............................ 585/259 X
4,260,840   4/1981  Puls et al. .......................... 585/259

FOREIGN PATENT DOCUMENTS 1418198  9/1969  Fed. Rep. of Germany ...... 585/259

*Primary Examiner*—Delbert E. Gantz
*Assistant Examiner*—A. Pal
*Attorney, Agent, or Firm*—Millen & White

[57] ABSTRACT

Process for selectively hydrogenating a diolefin present in a mixture of hydrocarbons having at least 4 carbon atoms per molecule: the hydrocarbon mixture is reacted with hydrogen in contact with a catalyst comprising palladium and silver, the molar ratio of hydrogen to the diolefin being from 1:1 to 5:1.

10 Claims, No Drawings

PROCESS FOR SELECTIVELY HYDROGENATING A DI-OLEFIN IN A MIXTURE OF HYDROCARBONS HAVING AT LEAST 4 CARBON ATOMS AND COMPRISING AN α-OLEFIN

The present invention relates to a process for selectively hydrogenating a diolefin in the presence of an α-olefin without substantial conversion of the α-olefin.

Processes for the high temperature conversion of hydrocarbons such as steam-cracking, viscosity reduction and catalytic cracking produce a great number of olefinic unsaturated hydrocarbons such as, for example, ethylene, propylene, 1-butene, cis- and trans-2-butenes, isobutene, n-pentenes, isopentenes, etc.

By way of example, a C$_4$ cut produced by steam-cracking contains a large proportion of butadiene mixed with 1-butene, 2-butenes and isobutene. Butadiene is separated from the corresponding olefins by, for example, extractive distillation in the presence of a solvent such as, for example, N-methyl pyrrolidone or dimethylformamide.

The olefinic cut thus separated may have, in the case of steam-cracking of naphtha, the following typical composition:

|  | BOILING POINT °C. | % b.w. |
| --- | --- | --- |
| Isobutane | −11.4 | 1.5 |
| Isobutene | −6.9 | 44.2 |
| 1-Butene | −6.3 | 28.0 |
| Butadiene | −4.4 | 0.3 |
| cis 2-Butene | +3.7 | 8 |
| n-Butane | −0.5 | 5.0 |
| trans 2-Butene | +0.9 | 13 |

The above Table also gives the boiling points of the hydrocarbons present in the cut. It is seen that certain hydrocarbons, for example, 1-butene, isobutene and butadiene, have very close boiling points.

If, for example, pure 1-butene and isobutene are desired, for example for chemical purposes, conventional separation processes are not adapted and it is necessary to use processes operated with selective chemical reactions; for example:

Selective hydrogenation of butadiene without isomerization of 1-butene; separation of isobutene by a process effecting selective dimerization of this hydrocarbon, selective etherification of isobutene with methanol (yielding methyl tert. butyl ether).

Isobutene can also be separated from the butene cut by isomerizing 1-butene to cis and trans 2-butenes which have boiling points not so close to that of isobutene and can thus be separated by superfractionation. This technique can be used when a maximum production of 2-butenes is desired.

However, there is an increasing demand for 1-butene, which compound is now used either as a monomer for producing poly-1-butene or as a comonomer for producing high density polyethylene.

These uses necessitate as complete a hydrogenation of butadiene as possible, the maximum tolerated amount of this compound being generally lower than 10 ppm by weight.

Under the conditions used for this hydrogenation and with conventional catalysts comprising group VIII metals such as Ni and Pd carried on various supports, there is observed, at these hydrogenation levels, a decrease of the 1-butene content due to butane formation, on the one hand, and to the migration of the double bond to form cis and trans 2-butenes, on the other hand. This is highly detrimental to the operation, leading to α-olefin yields substantially lower than 100%.

Various processes have been proposed to make the reaction more selective and increase the 1-butene yield. It has been proposed, for example, to hydrogenate butadiene in the presence of carbon monoxide in hydrogen. This technique requires the presence of large amounts of carbon monoxide in hydrogen, which is not always possible; the presence of carbon monoxide also results in a substantially lower catalytic hydrogenation activity.

The above statements also concern C$_5$ cuts from which the major portion of the diolefins has been removed by extraction: the last traces of diolefins can be removed by selective hydrogenation, and the latter must be effected with as low an isomerization of 1-pentene as possible.

The present invention has for an object to hydrogenate nearly completely the diolefin(s) without substantial isomerization of the 1-olefin, the parasitic polymerization reactions being largely avoided.

It is characterized in using a supported catalyst comprising palladium or a palladium compound and silver or a silver compound, the palladium content being from 0.05 to 0.5% by weight, the silver content from 0.05 to 1% by weight, and the molar ratio of hydrogen to the diolefins from 1/1 to 5/1.

The ratio by weight of silver to palladium is preferably from 0.7:1 to 3:1, particularly from 1:1 to 2.5:1.

The incorporation of the palladium and silver compounds can be effected by any of the known methods. It can be effected, for example, by impregnating the preformed (or not) carrier with a common solution of the metal compounds to be introduced, or with distinct solutions, for example, an aqueous solution containing one or more soluble palladium salts, such as palladium nitrate or chloride, and a solution of one or more soluble silver salts, for example, silver nitrate.

The palladium and silver metals can be incorporated together or successively. Between these operations, a drying and calcining treatment can be effected. The catalyst, after impregnation with the two metals, is then dried to eliminate the major portion of the impregnation solvent; it is finally calcined in air at a temperature from 200° to 900° C.

The reaction can be terminated, if necessary, with a reduction treatment, for example with hydrogen, according to a known technique. The reduction temperature is preferably from 0° to 200° C.

The preferred alumina carriers have a specific surface lower than 100 m$^2$/g, for example a surface of 1 to 100 m$^2$/g; they have preferably a low acidity.

Another example of carrier is silica, preferably silica having a surface of 10 to 200 m$^2$/g.

The selective hydrogenation can be effected at a temperature of about 0° to 160° C., in gas or liquid phase. In the latter case, the pressure must be sufficient to maintain a liquid phase and the preferred conditions are 0°–80° C., 3 to 20 bars and a feed rate of 2 to 50, preferably 10 to 30 liquid volumes per volume of catalyst per hour. In the gas phase, the feed rate of the C$_4$ cut (VVH gas) is, for example, 500 to 20,000 volumes per volume of catalyst per hour and the pressure, for example, 3 to 20 bars.

The preferred conditions comprise a liquid phase operation effected at low temperature, under which conditions the isomerization of the 1-olefin is strongly reduced, which gives the highest yields of 1-butene or 1-pentene.

The hydrogen/diolefins molar ratio is from 1/1 to 5/1, preferably from 1/1 to 2/1.

Hydrogen can be used in the pure state or diluted with inert gases such as, for example, nitrogen or methane.

EXAMPLE 1 (comparison)

A catalyst is prepared by impregnating an alumina carrier with a nitric solution of palladium nitrate, the carrier being present as pellets of 2 mm diameter, having a specific surface of 10 m$^2$/g and a pore volume of 0.6 cm$^3$/g, so as to obtain in the final catalyst a 0.3% b.w. content of palladium. After impregnation, the catalyst is dried at 120° C. in an oven and then calcined at 450° C. for 2 hours in an air stream.

The catalyst is placed in a tubular reactor and reduced in situ by passing hydrogen at 100° C. for 2 hours. The operating conditions are as follows:

| space velocity (liquid VVH): | 30 |
|---|---|
| pressure: | 10 bars |
| temperature: | 40° C. |
| H$_2$/butadiene: | 1.8 mole/mole |

The analyses of the charge and the resultant product are summarized in the following Table:

| COMPOUND | CHARGE (% b.w.) | PRODUCT (% b.w.) |
|---|---|---|
| 1-Butene | 28 | 26.04 |
| cis 2-Butene | 8 | 8.67 |
| tr 2-Butene | 13 | 14.09 |
| Butadiene | 0.3 | ≦10 ppm |
| Isobutene | 44.2 | 44.2 |
| Butane | 5 | 5.5 |
| Isobutane | 1.5 | 1.5 |
| Polymers | Nil | 100 ppm |

The yield of product is practically 100% b.w. It is found that the catalyst is sufficiently active since it fully converts butadiene. However the yield of 1-butene is 26.04/28, thus only 93%; the 1-butene loss thus amounts to 7%.

EXAMPLE 2 (according to the invention)

A catalyst is prepared by impregnating an alumina carrier identical to that of example 1 with a nitric solution of palladium nitrate and silver nitrate. The catalyst is dried and calcined as in example 1; it contains 0.3% b.w. of palladium and 0.3% b.w. of silver.

The catalyst is then fed into a tubular reactor and reduced as in example 1. The charge and the operating conditions are the same as in example 1. The resultant product has the following composition:

| COMPOUND | PRODUCT (% b.w.) |
|---|---|
| 1-Butene | 27.24 |
| cis 2-Butene | 8.24 |
| tr 2-Butene | 13.42 |
| Butadiene | ≦10 ppm |
| Isobutene | 44.2 |
| Butane | 5.4 |
| Isobutane | 1.5 |
| Polymers | ≦20 ppm |

The yield of product is practically 100% b.w.

It is found that the catalyst has the same activity as in example 1; however its selectivity is better since 1-butene is present in the product in an amount which is nearly that of the charge (27.24% against 28%). The 1-butene yield is 27.24/28, thus 97.3%, which represents a loss of 2.7% which is far lower than observed in the presence of the catalyst comprising palladium alone.

EXAMPLE 3 (according to the invention)

The operation is as in example 2, except that the amount of silver is decreased. The resultant catalyst contains 0.3% b.w. of palladium and 0.05% b.w. of silver.

The catalyst is then charged into a tubular reactor and reduced as in example 1. The charge and the operating conditions are the same as in example 1. The properties of the charge and the product are given in the following Table:

| COMPOUND | CHARGE (% b.w.) | PRODUCT (% b.w.) |
|---|---|---|
| 1-Butene | 28 | 26.40 |
| cis 2-Butene | 8 | 8.5 |
| tr 2-Butene | 13 | 13.9 |
| Butadiene | 0.3 | ≦10 ppm |
| Isobutene | 44.2 | 44.2 |
| Butane | 5 | 5.5 |
| Isobutane | 1.5 | 1.5 |
| Polymers | Nil | 100 ppm |

The yield by weight of product is practically 100%. The catalyst is sufficiently active but its selectivity to 1-butene conversion is substantially lower than in example 2; the 1-butene yield is 94.3% instead of 97.3% in example 2 wherein the silver content is equivalent by weight to the palladium content. This value of 94.3% is however higher than obtained in example 1 with the catalyst of palladium alone (93%).

EXAMPLE 4 (according to the invention)

A catalyst is prepared as in example 2; however, instead of an alumina carrier, there is used silica as pellets of 3 mm diameter, having a specific surface of 90 m$^2$/g and a total pore volume of 0.8 cm$^3$/g.

The operation is then effected as in example 1.

The product obtained after hydrogenation has the following composition:

| COMPOUND | PRODUCT (% b.w.) |
|---|---|
| 1-Butene | 27.26 |
| cis 2-Butene | 8.22 |
| tr 2-Butene | 13.40 |
| Butadiene | ≦10 ppm |
| Isobutene | 44.20 |
| Butane | 5.32 |
| Isobutane | 1.50 |
| Polymers | ≦20 ppm |

The yield of product is practically 100% b.w.

The 1-butene yield is 97.35%, thus practically the same as in example 2.

EXAMPLE 5 (according to the invention)

The catalyst of example 2 is used to treat a C$_5$ hydrocarbons cut from catalytic cracking. It is found that the diolefins hydrogenate without substantial isomerization of the double bond of the terminal mono-olefins.

What is claimed is:

1. In a process for selectively hydrogenating a diolefin present in a mixture of hydrocarbons having at least 4 carbon atoms and comprising an 1-olefin in addition to the diolefin, wherein said mixture is reacted with hydrogen in contact with a catalyst, the improvement wherein said catalyst is a supported catalyst comprising simultaneously palladium or a palladium compound and silver or a silver compound, the palladium content of the catalyst being from 0.05 to 0.5% by weight and the silver content from 0.05 to 1% by weight, the $$\frac{silver}{palladium} \text{ ratio}$$

being from 0.7:1 to 3:1 by weight, thereby avoiding substantial isomerization and hydrogenation of the 1-olefin.

2. A process according to claim 1, wherein the hydrogen/diolefin molar ratio is from 1/1 to 2/1.

3. A process according to claim 1 wherein the $$\frac{silver}{palladium} \text{ ratio}$$

is from 1:1 to 2.5:1 by weight.

4. A process according to claim 1, wherein the carrier is alumina of specific surface lower than 100 $m^2/g$.

5. A process according to claim 1, wherein the carrier is silica of specific surface between 10 and 200 $m^2/g$.

6. A process according to claim 1 wherein the hydrocarbon mixture is a $C_4$ cut comprising butadiene and 1-butene.

7. A process according to claim 1 wherein the operation is effected in liquid phase at 0°–80° C. under 3–20 bars at a liquid feed rate of 2 to 50 volumes per volume of catalyst per hour.

8. A process according to claim 1 wherein the catalyst is obtained by incorporating the palladium and silver catalytic metals to the carrier and then calcining in air at 200°–900° C.

9. A process according to claim 8, wherein calcining is followed with a hydrogen reduction at 0°–200° C.

10. A process according to claim 1, wherein the hydrogen/diolefin molar ratio is from 1/1 to 5/1.

* * * * *